(12) United States Patent
Glickel

(10) Patent No.: US 11,350,975 B2
(45) Date of Patent: Jun. 7, 2022

(54) DISTAL RADIUS VOLAR LOCKING PLATE WITH EXTENSION FOR ULNAR VOLAR FRAGMENT

(71) Applicant: Steven Glickel, New York, NY (US)

(72) Inventor: Steven Glickel, New York, NY (US)

( * ) Notice: Subject to any disclaimer, the term of this patent is extended or adjusted under 35 U.S.C. 154(b) by 696 days.

(21) Appl. No.: 14/227,155

(22) Filed: Mar. 27, 2014

(65) Prior Publication Data
US 2014/0214089 A1   Jul. 31, 2014

Related U.S. Application Data

(63) Continuation of application No. 13/246,211, filed on Sep. 27, 2011, now Pat. No. 9,220,549.

(51) Int. Cl.
*A61B 17/80* (2006.01)
*A61B 17/82* (2006.01)

(52) U.S. Cl.
CPC ........ *A61B 17/8061* (2013.01); *A61B 17/809* (2013.01); *A61B 17/82* (2013.01); *Y10T 29/49826* (2015.01)

(58) Field of Classification Search
CPC . A61B 17/80; A61B 17/8004; A61B 17/8061; A61B 17/8085; A61B 17/809; A61B 17/82; Y10T 29/49826
USPC ........................................................ 606/281
See application file for complete search history.

(56) References Cited

U.S. PATENT DOCUMENTS

| | | | |
|---|---|---|---|
| 4,651,724 A | 3/1987 | Brerntey et al. | |
| 5,674,222 A | 10/1997 | Berger | |
| 6,283,969 B1 | 9/2001 | Grusin et al. | |
| 6,607,536 B2 | 8/2003 | Litwin | |
| 6,712,820 B2 * | 3/2004 | Orbay | A61B 17/68 606/286 |
| 7,189,237 B2 * | 3/2007 | Huebner | A61B 17/1728 606/291 |
| 7,250,053 B2 * | 7/2007 | Orbay | A61B 17/8057 606/291 |

(Continued)

FOREIGN PATENT DOCUMENTS

| | | | | |
|---|---|---|---|---|
| EP | 2564797 A1 * | 3/2013 | ......... | A61B 17/8061 |
| WO | 2003041416 | 6/2003 | | |
| WO | 2005034780 | 4/2005 | | |

OTHER PUBLICATIONS

Jorge Orbay, "Volar Plate Fixation of Distal Radius Fractures", Hand Clin 21 (2005) 347 . . . 354.

*Primary Examiner* — Marcela I. Shirsat
(74) *Attorney, Agent, or Firm* — Polsinelli PC

(57) ABSTRACT

A distal radius fixation plate for volar plating may comprise a distal radius fixation plate body configured to be placed adjacent a fractured volar distal radius and proximal to a watershed line of the volar distal radius and a distal radius fixation plate extension approximately 60 to 80% thinner on average than the distal radius fixation plate and projecting from the distal radius fixation plate body and configured to be placed so that it extends distal to the watershed line, the plate extension configured to curve around an ulnar/volar corner of the distal radius bone so as to engage the volar lip preferably without curving around other parts of the volar lip of the distal radius. The plate extension may have a hook at its upper end. The plate body may have an obliquely angled screw hole to buttress a radial styloid fragment.

25 Claims, 5 Drawing Sheets

(56) References Cited

U.S. PATENT DOCUMENTS

| | | | |
|---|---|---|---|
| 7,655,029 B2 | 2/2010 | Niederberger et al. | |
| 8,790,378 B2 * | 7/2014 | Castaneda | A61B 17/8061 606/285 |
| 8,961,574 B2 * | 2/2015 | Bluechel | A61B 17/8061 606/281 |
| 9,283,010 B2 * | 3/2016 | Medoff | A61B 17/8061 |
| 2002/0032446 A1 * | 3/2002 | Orbay | A61B 17/7208 606/286 |
| 2005/0010226 A1 | 1/2005 | Grady, Jr. et al. | |
| 2005/0234458 A1 * | 10/2005 | Huebner | A61B 17/8061 606/71 |
| 2008/0161861 A1 * | 7/2008 | Huebner | A61B 17/8085 606/286 |
| 2009/0275991 A1 | 11/2009 | Medoff | |
| 2010/0137866 A1 | 6/2010 | Gelfand | |
| 2011/0152943 A1 * | 6/2011 | Gonzalez-Hernandez | A61B 17/8061 606/286 |
| 2013/0060251 A1 | 3/2013 | Eglseder, Jr. | |
| 2013/0204307 A1 * | 8/2013 | Castaneda | A61B 17/8061 606/297 |
| 2013/0245699 A1 * | 9/2013 | Orbay | A61B 17/8061 606/286 |

\* cited by examiner

ANTERIOR

LATERAL

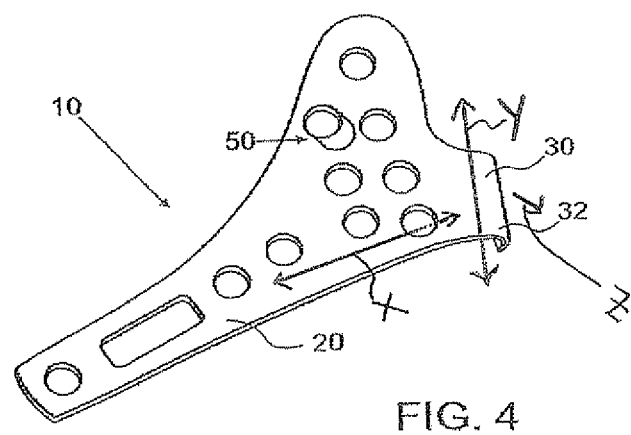
FIG. 4
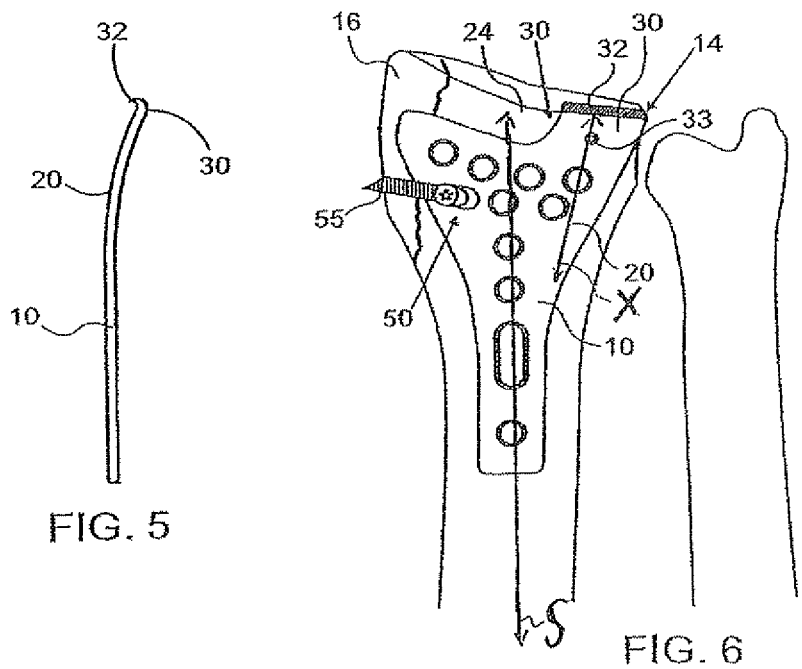
FIG. 5
FIG. 6

METHOD - 200

POSITIONING A DISTAL RADIUS FIXATION PLATE BODY OF A DISTAL RADIUS FIXATION PLATE ALONGSIDE A VOLAR DISTAL RADIUS OF THE FRACTURED DISTAL RADIUS SO THAT THE DISTAL RADIUS FIXATION PLATE BODY IS PROXIMAL TO THE WATERSHED LINE OF THE DISTAL RADIUS, AND SO THAT A PLATE EXTENSION THAT PROJECTS FROM THE DISTAL RADIUS FIXATION PLATE BODY AND THAT IS AT LEAST 20% THINNER ON AVERAGE THAN THE PLATE BODY, EXTENDS DISTAL TO THE WATERSHED LINE ~210

FIG. 7

| METHOD - 300 |

MANUFACTURING A DISTAL RADIUS FIXATION PLATE BODY AND A PLATE EXTENSION OF A DISTAL RADIUS FIXATION PLATE AS ONE INTEGRAL PRODUCT OF A MOLD — 310

MANUFACTURING THE DISTAL RADIUS FIXATION PLATE EXTENSION TO BE AT LEAST 20% THINNER ON AVERAGE THAN THE DISTAL RADIUS FIXATION PLATE BODY — 320

MANUFACTURING A CONTINUOUS WIDTH OF THE HOOKED DISTAL END TO BE AT LEAST HALF AS WIDE AS THE PLATE EXTENSION AT ANY POINT ALONG A LENGTH OF THE PLATE EXTENSION — 330

INTEGRALLY JOINING A PROXIMAL END OF THE PLATE EXTENSION TO AT LEAST A THIRD OF A WIDTH OF A DISTAL END OF THE PLATE BODY SUCH THAT AT LEAST A MAJORITY OF A WIDTH OF THE PLATE EXTENSION IS INTEGRALLY JOINED TO THE DISTAL END OF THE PLATE BODY — 340

MANUFACTURING THE HOOKED DISTAL END SO THAT THE HOOKED DISTAL END CURVES MORE THAN 90 ROTATIONAL DEGREES AND LESS THAN 120 ROTATIONAL DEGREES — 350

FIG. 8

| METHOD - 400 |
|---|

| POSITIONING A DISTAL RADIUS FIXATION PLATE BODY OF A DISTAL RADIUS FIXATION PLATE ALONGSIDE A VOLAR DISTAL RADIUS OF THE FRACTURED DISTAL RADIUS SO THAT THE DISTAL RADIUS FIXATION PLATE BODY IS PROXIMAL TO THE WATERSHED LINE OF THE DISTAL RADIUS, AND SO THAT A PLATE EXTENSION THAT PROJECTS FROM THE DISTAL RADIUS FIXATION PLATE BODY AND THAT IS AT LEAST 20% THINNER ON AVERAGE THAN THE PLATE BODY, EXTENDS DISTAL TO THE WATERSHED LINE |
|---|

↓ 410

| POSITIONING THE PLATE EXTENSION SO AS TO CURVE AROUND AND BUTTRESS THE ULNAR VOLAR CORNER OF THE DISTAL RADIUS WITHOUT CURVING AROUND OTHER PARTS OF A VOLAR LIP OF THE DISTAL RADIUS, THE PLATE EXTENSION ANCHORED TO AN ULNAR VOLAR FRAGMENT |
|---|

↓ 420

| POSITIONING THE PLATE EXTENSION SO THAT A CONTINUOUS WIDTH OF THE HOOKED DISTAL END OF THE PLATE EXTENSION CURVES MORE THAN 90 ROTATIONAL DEGREES AND ENGAGES THE VOLAR LIP ACROSS AT LEAST A MAJORITY OF A WIDTH OF THE ULNAR/VOLAR CORNER |
|---|

DISTAL RADIUS VOLAR LOCKING PLATE WITH EXTENSION FOR ULNAR VOLAR FRAGMENT

CROSS-REFERENCE TO RELATED APPLICATION

This application is a continuation of and claims the benefit of U.S. patent application Ser. No. 13/246,211 filed on Sep. 27, 2011 and is now issued as now issued as U.S. Pat. No. 9,220,549, which is incorporated by reference in its entirety.

FIELD AND BACKGROUND OF THE INVENTION

The present invention relates to apparatuses and methods used in medical treatment of a distal radius fracture, and, more particularly, to such apparatuses and methods in which an extension from a volar fixation plate beyond the watershed line is used.

The forearm has two large bones, the radius and the ulna, which run parallel to one another. The proximal end of the radius is at the lateral side of the elbow and extends all the way to the thumb side of the wrist which is the distal end of the radius (from a reference position in which the palm of the hand faces forward). The radius can also be divided in its other dimensions. For example the palm side of the radius bone is called the "volar" and the other side is called "dorsal". The volar distal radius therefore refers to the palm side of the distal radius. The most prominent region (the part that sticks out like a ridge line) of the volar distal radius is called the "watershed line". A distal radius fracture is a common bone fracture of the distal end of the radius in the forearm, next to the wrist joint. FIG. 1 shows a "watershed line" 15 across a distal radius.

Surgical implanatation of a fixation plate to guide healing of the bone has helped revolutionize treatment of distal radius injuries. The plate is fixed adjacent to the bone to be healed and is held in place using screws. There are many different techniques for treating distal radius fractures including dorsal plating, fragment specific fixation, non-spanning external fixation, volar plating, spanning internal fixation plates.

Locked volar plating is a commonly used technique that has significantly improved the value of treatment by offering a patient with a distal radius fracture early return to work, normal lifestlye, etc. The volar fixation plate is implanted in the body and placed adjacent to but external to the volar side of the radius bone. The volar plate has holes and is affixed by screws that run through holes in the plate. There are two types of screws which are used with these plates, non-locking and locking. Non-locking screws are like traditional screws with a normal appearing head. They only fix to the bone and not to the plate. Locking screws have a smaller diameter head which is threaded. The head of a locking screw locks to the plate within the hole in the plate. Locking and non-locking screws typically run perpendicular or within a range of approximately 15 degrees from perpendicular to a surface of the plate i.e. they can have a somewhat variable angle within which they can lock to the plate.

Notwithstanding its value, a well known complication of volar plating is irritation and/or rupture of the tendons, especially flexor tendons. The idea is to keep the bone fragments of the fracture together securely without causing irritation or rupture of the tendons. The most common way to position the volar plate is to position it at or just proximal to the watershed line of the distal radius, as shown in FIG. 3 (prior art). This has the advantage that it minimizes the risk of flexor tendon irritation that arises if the plate is distal to the watershed line. An alternative place to position the plate is distal to the watershed line of the distal radius, as shown in FIG. 2 (prior art).

There is a well known concern the art to avoid having volar fixation plates project beyond or above the watershed line. For example, as advocated by a prominent orthopaedic surgeon, in Volar Plate Fixation of Distal Radius Fractures by Jorge Orbay, M.D., Hand Clinic 21 (2005) 347-354 at page 348, it states that a "properly designed volar plate must provide sufficient distal buttressing to control the volar marginal fragemnt but must not project beyond or above the watershed line to prevent contact with flexor tendons." Since flexor tendons pass directly over the watershed line, they can be chronically irritated by the metal plate and ultimately rupture if the plate is distal to the watershed line. In fact, the Journal of Bone and Joint Surgery reported that a more distally placed plate is associated with a 4% risk of flexor tendon rupture compared to 0% for a more proximally placed plate design. Flexor tendon rupture is a serious and dreaded complication of distal radius fixation, and is occurring with greater frequency since the advent of volar locking plates (although it can also occur as a complication of dorsal plating if a screw protrudes through the volar cortex of the radius).

However, when the distal radius fracture has small bone fragments, for example in the volar/ulnar corner, many orthopaedic surgeons feel that a plate proximal to the watershed line will not capture the fragment so it is necessary to put the volar locking plate distal to the watershed line or add additional forms of fixation to support these small but very important bone fragments at the distal part of the fracture, especially at the volar/ulnar corner. The small bone fragments at the ulnar/volar corner are critical for joint stability. The volar/ulnar corner is hard to buttress or secure with a screw. However, Dr. Orbay, the previously mentioned orthopedic surgeon who advocates positioning the volar plate proximal to the watershed line maintains that the preferred position of the volar plate is proximal to the watershed line even in the case of small volar rim bone fragments since he maintains that these small bone fragments can be adequately supported by use of a K-wire technique. However, if K-wires are used in volar plating the wrist must be immobilized until the fracture is adequately healed, which is usually 6 weeks in contrast to the 2 weeks required if rigid fixation with a plate and/or screws is used. K-wires can also be potential passages for bacteria, can break or bend, can lose fixation and can migrate. In addition, for very small but critical bone fragments, the K-wire technique is not entirely effective because it does not provide rigid fixation like a screw does.

There is a compelling need to have a distal radius fixation plate that avoids flexor tendon irritation but which is secure enough to provide fixation for the small but very important bone fragments of the volar/ulnar corner of the radius that are critical for joint stability and to do so without the disadvantages of the prior art.

SUMMARY OF THE PRESENT INVENTION

One aspect of the present invention is a method of volar plate fixation on a fractured distal radius, comprising positioning a distal radius fixation plate body of a distal radius fixation plate alongside a volar distal radius of the fractured distal radius so that the distal radius fixation plate body is proximal to the watershed line of the distal radius, and so that a plate extension that projects from the distal radius fixation plate body and that is at least 20% thinner on average than the plate body, extends distal to the watershed line.

A further aspect of the present invention is a method of manufacturing a distal radius fixation plate, comprising manufacturing a distal radius fixation plate body and a plate extension of a distal radius fixation plate as one integral product of a mold; manufacturing the distal radius fixation plate extension to be at least 20% thinner on average than the distal radius fixation plate body; manufacturing a continuous width of the hooked distal end to be at least half as wide as the plate extension at any point along a length of the plate extension; integrally joining a proximal end of the plate extension to at least a third of a width of a distal end of the plate body such that at least a majority of a width of the plate extension is integrally joined to the distal end of the plate body; and manufacturing the hooked distal end so that the hooked distal end curves more than 90 rotational degrees and less than 120 rotational degrees.

A still further aspect of the present invention is a method of volar plate fixation on a fractured distal radius, comprising positioning a distal radius fixation plate body of a distal radius fixation plate alongside a volar distal radius of the fractured distal radius so that the distal radius fixation plate body is proximal to the watershed line of the distal radius, and so that a plate extension that projects from the distal radius fixation plate body and that is at least 20% thinner on average than the plate body, extends distal to the watershed line; positioning the plate extension so as to curve around and buttress the ulnar volar corner of the distal radius without curving around other parts of a volar lip of the distal radius, the plate extension anchored to an ulnar volar fragment; and positioning the plate extension so that a continuous width of the hooked distal end of the plate extension curves more than 90 rotational degrees and engages the volar lip across at least a majority of a width of the ulnar/volar corner.

One further aspect of the present invention is a distal radius fixation plate for volar plating, comprising a distal radius fixation plate body configured to be placed adjacent a fractured volar distal radius and proximal to a watershed line of the volar distal radius; and a distal radius fixation plate extension which is at least 20% thinner on average than the distal radius fixation plate and projecting from the distal radius fixation plate body and configured to be placed so that it extends distal to the watershed line, the plate extension configured to curve around an ulnar/volar corner of the distal radius bone without curving around other parts of the volar lip of the distal radius.

A further aspect of the present invention is a distal radius fixation plate, comprising a distal radius fixation plate body configured to be placed adjacent a fractured volar distal radius and proximal to a watershed line of the volar distal radius, the distal radius fixation plate body having an obliquely angled screw hole alongside a proximal portion of a radial styloid fragment; and a distal radius fixation plate extension thinner than and projecting from the distal radius fixation plate body and configured to be placed so that it extends distal to the watershed line at the ulnar volar corner of the distal radius bone.

A still further aspect of the present invention is a method of volar plate fixation on a fractured distal radius bone, comprising positioning a distal radius fixation plate body alongside a volar distal radius of the fractured distal radius bone so that the distal radius fixation plate is proximal to the watershed line of the distal radius bone, the distal radius fixation plate having a plate body and a plate extension, the plate extension at least 20% thinner on average than the plate body; and anchoring the plate extension to an ulnar volar fragment by positioning the plate extension so that it protrudes distal to the watershed line at the ulnar volar corner of the distal radius bone.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 4 is an oblique view of a distal radius plate, in accordance with one embodiment of the present invention;

FIG. 5 is a side view in schematic form of the distal radial plate of FIG. 4, in accordance with a further embodiment of the present invention;

FIG. 6 is a front view of a distal radial plate positioned over a distal radius bone, in accordance with one embodiment of the present invention;

FIG. 7 is a flow chart showing a method in accordance with one embodiment of the present invention;

FIG. 8 is a flow chart showing a further method in accordance with one embodiment of the present invention; and FIG. 9 is a flow chart showing a further method in accordance with one embodiment of the present invention.

DETAILED DESCRIPTION OF THE INVENTION

Figure 1A:
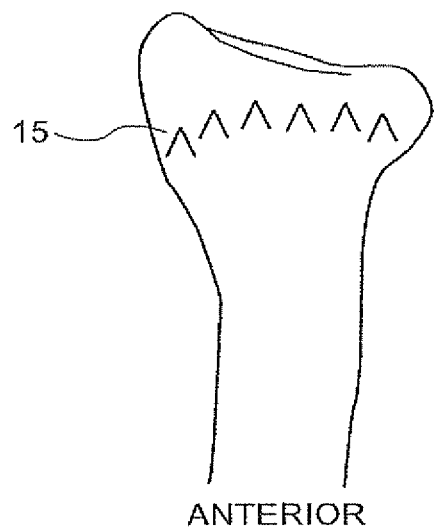
FIGS. 1A and 1B are anterior and lateral schematic views, based on photographs, of a distal radial model designating the watershed line using arrowheads.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a distal radius fixation plate that may include a distal radius fixation plate body that may be configured to be placed proximal to a watershed line of a volar distal radius as well as a distal radius fixation plate extension that may be approximately 60% to 80% as thick on average as the distal radius fixation plate body. The extension plate may project from the distal radius fixation plate body and may be configured to be placed so that it extends distal to the watershed line. The extension plate may also be configured to protrude alongside an ulnar/volar corner of the distal radius bone. The extension plate may have an upper end having a hooked cross-section. The hook may curve around a little more than 90 degrees (approximately 100 to 110 rotational degrees in some preferred embodiments) so as to engage the volar lip of the distal radius. The hook may wrap around the distal edge of the ulnar/volar corner. In preferred embodiments, the extension plate may not protrude past the watershed line into other parts of the volar distal radius besides the ulnar/volar corner. A screw may be used to further buttress the extension plate. In addition, the distal radius fixation plate body may have an obliquely angled hole such as a recessed screw hole alongside a proximal portion of a radial styloid fragment to provide fixation of that fragment without the need for a separate fixation device in addition to the plate.

In contrast to prior art fixation plates for distal radius fractures in which the plate is situated either proximal or distal to the watershed line, the fixation plate of the present invention may be situated proximal to the watershed line while simultaneously having a plate extension that may be situated distal to the watershed line. In contrast to prior art fixation plates in which the fixation plate is situated proximal to the watershed line and is not effective in treating fractures having an ulnar volar corner fragment, the fixation plate of the present invention may include an extension that is designed to buttress the ulnar volar corner fragment. While being secure enough to buttress the ulnar volar corner, the volar fixation plate of the present invention may simultaneously avoid tendon irritation. In further contrast to prior art fixation plates for distal radius fractures in which the plate extends distal to the watershed line but the plate carries a significant increased risk of flexor tendon irritation, the distal radius fixation plate of the present invention may avoid increased risk of flexor tendon irritation even though it may have an extension that may extend distal to the watershed line. For one thing, the extension plate may be made thinner than the body of the fixation plate in order to minimize the volume of material beyond the watershed line. For example, it may be approximately 20-40% thinner on average. In further contrast to the prior art fixation plates, which may not have a hooked cross-section designed to buttress the ulnar volar corner fragment, the fixation plate of the present invention may include an extension plate that may be configured to have a hook at the distal end so as to further anchor fragments in the ulnar volar corner. In still further contrast to prior art fixation plates in which screws may be perpendicular to the body of the plate, in some preferred embodiments the fixation plate of the present invention may include a screw positioned into an obliquely angled screw hole to further buttress a radial styloid fragment. In still further contrast to the prior art fixation plates, which may primarily rely on screws or K-wires to secure the ulnar volar corner while leaving the plate body proximal to the watershed, but which may thereby risk migration or loss of fixation of the screw or K-wire, breakage or the creation of a passage for bacteria, the plate extension with a hooked upper end may avoid these complications while still minimizing or avoiding tendon irritation and being secure enough to buttress the ulnar volar corner. In addition, the K-wire fixation of the prior art is not rigid so the wrist would have to be immobilized for approximately 6 weeks whereas the rigid fixation of the plate and hooked plate extension of the present invention may only require 2 weeks of immobilization. In contrast to prior art fixation plates used for other bones, which if applied to the distal radius, any curved portion would disturb or damage the articular cartilage at the distal end of the distal radius, the distal radius fixation plate and method of the present invention may be used without irritating or damaging this articular cartilage.

The principles and operation of a distal radius fixation plate with extension for ulnar volar fragment, according to the present invention may be better understood with reference to the drawings and the accompanying description.

The terms "about" and "approximately" as used in this patent application mean plus or minus 10%.

Figure 1B:
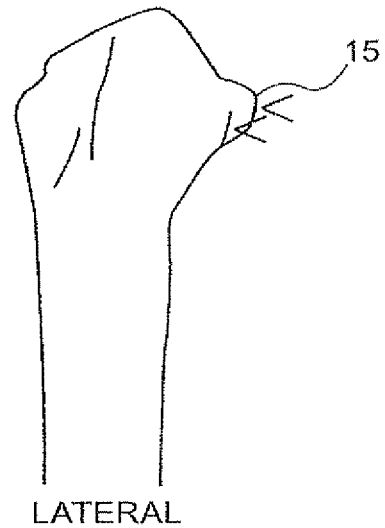

FIGS. 1A and 1B are anterior and lateral photographs of a distal radial model designating the watershed line using arrowheads as they appeared in the Journal of Bone & Joint Surgery Volume 93A Number 4 Feb. 16, 2011 as part of an article entitled "Volar Locking Plate Implant Prominence and Flexor Tendon Rupture".

As seen from FIG. 4, a distal radius fixation plate 10 may comprise a distal radius fixation plate body 20 configured to be placed adjacent a fractured volar distal radius (i.e. a fractured distal radius on the volar side of the radius) and proximal to the watershed line 22 (see FIG. 1) of the volar distal radius 24. As seen from FIG. 1A-B, the watershed line 22 is the most prominent part of the volar distal radius 24—it sticks out like a ridge. Plate 10 may be a volar plate in that it may be configured to be positioned alongside the volar radius. Plate 10 may also include a distal radius fixation plate extension 30 that may be thinner on average than the distal radius fixation plate body 20 and that may project distally from distal radius fixation plate body 20.

Figure 2:
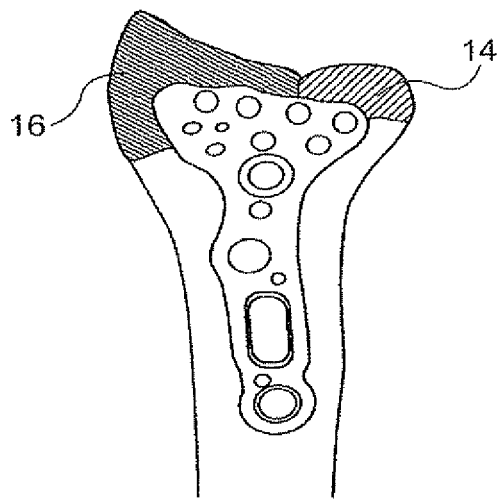
FIG. 2 is a schematic view, based on a photograph, of a prior art left volar distal radial plate at the position of best fit on a model distal to the watershed line.
Figure 3:
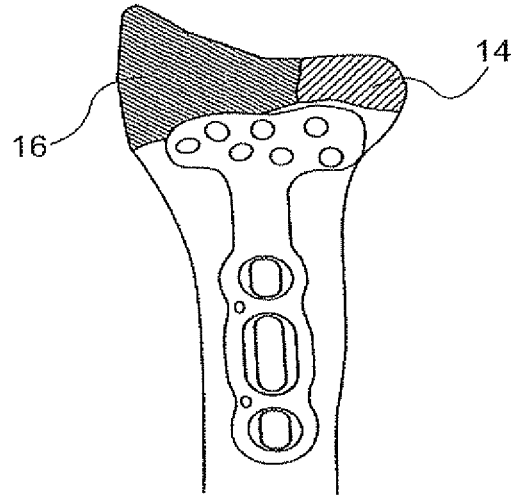
FIG. 3 is a schematic view, based on a photograph, of a prior art left volar distal radial plate, different from FIG. 3, at its position of best fit on a model proximal to the watershed line.

As shown in FIGS. 2 and 3, the area distal to the watershed line of the distal radius fracture may include the ulnar volar corner 14 (see FIG. 3 and FIG. 6) and the radiual styloid fragment 16 (see FIG. 2).

Extension 30 may be configured so that it may be positioned so as to extend distal to the watershed line 22 (see watershed line in FIGS. 1A-1B) Extension 30 may in particular be configured so that it may be positioned distal to the watershed line 22 at the ulnar volar corner of the distal radius bone. Extension 30 may also be configured so as to be positioned adjacent the ulnar/volar corner so as to curve around the ulnar/volar corner of the distal radius bone. In some preferred embodiments, the extension 30 may curve around the ulnar/volar corner without curving around or protruding alongside other parts of the volar lip of the distal radius. Accordingly, plate extension 30 may thereby extend distal to the watershed line only at the ulnar volar corner, for example not at the radial styloid.

Having the plate extension 30 curve around the ulnar volar corner may be accomplished by configuring the shape of the plate extension 30. As seen from FIG. 4, the width of the plate extension 30 may be said to lie substantially along a horizontal axis Y shown in FIG. 4. FIG. 4 also shows that plate extension 30 may be curved all along its length. In that case, the curved "length" includes a generally longitudinal direction or axis, X, which axis X lies on a plane that, when applied on a standing patient whose arms extend downward, is a substantially sagittal plane, as shown in FIG. 4 and in FIG. 6 (the substantially sagittal plane may be at an approximately 25 degree angle from a true sagittal plane, S, as shown in FIG. 6). This curved length of plate extension 30 may have a Z component in a Z axis (see FIG. 4) perpendicular to the X axis (longitudinal) and to the Y (width) axis shown in FIG. 4 (which Z component may be greatest at the hooked distal end 32 of plate extension 30). In other preferred embodiments, at least 90 percent of plate extension 30 is curved and in other preferred embodiments, at least two-thirds of the plate extension 30 is curved.

As seen from FIG. 5, distal radius fixation plate extension 30 may comprise a hook or may have an upper end 32 that may be hooked and as such may have a hooked cross-section (as seen in FIG. 5). The hooked upper end 32 may be configured to curve around somewhat more than 90 rotational degrees so as to engage a volar lip of the distal radius. In some preferred embodiments, hooked distal end 32 of extension 30 may curve around between approximately 95 and 115 rotational degrees, and in other preferred embodiments, between 100 and 110 rotational degrees, which would allow it to engage the volar lip. The hooked distal end 32 may be configured to curve around or wrap around the ulnar volar corner and engage the volar lip of the distal radius. Plate extension 30 may also be said to have distal end 32 that may be configured to wrap around a distal edge of the ulnar volar corner.

In one preferred embodiment, hooked distal end 32 curves more than 90 rotational degrees and not more than 120 rotational degrees relative to a remainder of the plate extension, and preferably relative to a distal end of the remainder of the plate extension 30 (the remainder being the part of plate extension 30 other than hooked distal end 32), so as to curve around and engage the volar lip at the ulnar/volar corner. As a result of not curving more than 120 rotational degrees, and in more preferred embodiments not curving more than 115 rotational degrees, or in other preferred embodiments not curving more than 110 rotational degrees or 105 or 100 rotational degrees, the hooked distal end 32, and preferably a continuous uninterrupted width of hooked distal end 32, may engage the volar lip across the ulnar/volar corner by following a contour of a curve of the volar lip (including at a distal end of the distal radius) without such curving of the hooked distal end extending the hooked distal end into a distal end of the distal radius. Extending the hooked distal end into the distal end of the radius would be expected to disturb and damage the articular cartilage and harm therapeutic outcome. In contrast, the articular cartilage at the distal end of the distal radius may not have to be irritated (or worse, damaged) for the present invention to function properly as needed. Hooked distal end 32, and preferably a continuous width of hooked distal end 32, in a preferred embodiment follows a contour of the entire curved length of the volar lip, or in other preferred embodiments, follows a contour along at least two-thirds of the curve, or on still other preferred embodiments, along at least a majority of, the curve of the volar lip.

As can also be seen from FIG. 4, plate extension 30 may be described as comprising hooked distal end 32 plus a remainder of the plate extension 30 other than hooked distal end 32. FIG. 4 and FIG. 6 show that in a preferred embodiment, plate extension 30 is integrally joined to the plate body 20 across the entire width of the plate extension at the most proximal part of plate extension 30. Plate extension 30 may, in certain preferred embodiments, be integrally joined to the plate body 20 across at least 90% of (or in other preferred embodiments across at least two-thirds of) the width of the plate extension at the most proximal part of plate extension 30. In the preferred embodiment shown in FIG. 4, the most proximal part of plate extension 30 is also the widest part of the plate extension 30, although in other embodiments a widest part of plate extension 30 may be more distal.

FIGS. 4-6 show that in a preferred embodiment a width, which may be a continuous width, of the hooked distal end 32 may be configured to engage the volar lip across at least a majority of the width of the ulnar/volar corner, and in other preferred embodiments across at least two-thirds of the width of the ulnar volar corner, and in still other preferred embodiments, as shown in FIG. 6, across an entire width of the ulnar volar corner. The continuous width of the hooked distal end may do so by following a contour of a curve of the volar lip. In a preferred embodiment, the continuous width of the hooked distal end 32 is at least half as wide as the plate extension at any point along a curved length of the plate extension. In the preferred embodiment shown in FIG. 4, hooked distal end 32 is at least two-thirds as wide as plate extension 30 at any point along the curved length of plate extension 30.

The drawings are not intended to show every subtle detail. For example, although not readily apparent from FIG. 4, in a preferred embodiment, from around the bottom of the fourth circular hole (counting such holes from the bottom of the plate 10 upward toward the extension 30), the plate body 20 bulges out of the page toward the viewer (to conform to the distal radius), as seen from FIG. 5, and then just proximal to the Y axis the plate extension 30 curves back toward the page and away from the viewer, as shown in FIG. 4.

So as to minimize material and thereby minimize the risk of tendon irritation and rupture while still being able to securely hold the ulnar volar corner fragments, plate 10 has a plate extension 30 that may be at least 20% less thick on average (or in other preferred embodiments at least 25% or at least 30% or at least 35% or at least 40% less thick on average) than the average thickness of the distal radius fixation plate body 20. In some preferred embodiments, the plate extension 30 may have an average thickness of between 50% and 70%, or in some preferred embodiments, of between 60% to 80% or between 50% to 80% of the average thickness of the distal radius fixation plate body 20. In other preferred embodiments, the plate extension 30 may have an average thickness of no more than 70% an average thickness of the distal radius fixation plate body 20 of the fixation plate, or the plate extension may have an average thickness of no more than 55% or no more than 60% or no more than 65% or or no more than 75% or no more than 80% of the average thickness of the distal radius fixation plate body 20.

In terms of the absolute thickness on average, the plate body 20 may have an average thickness of between 1.5 mm and 2.0 mm or in some preferred embodiments of between 1.5 mm and 1.7 mm. In some preferred embodiments, the plate body 20 may have an average thickness of 1.6 mm or 1.7 mm or 1.8 mm or 1.9 mm. The plate extension 30 may on average be 50 to 80 percent or in some preferred embodiments 60% to 80% or 50% to 70% as thick as the plate body 20 and therefore may have an average thickness of between 0.8 millimeters and 1.4 millimeters or in other preferred embodiments of between 0.8 mm and 1.4 mm or from 0.8 mm to 1.0 mm or in still other preferred embodiments of between 1.05 mm and 1.4 mm. In still some preferred embodiments, especially where plate body 20 has an average thickness of 1.6 mm, the plate extension 30 may have an average thickness of between 1.0 mm to 1.2 mm (or in some embodiments between 0.8 mm and 1.2 mm) or in other preferred embodiments of between 1.0 mm and 1.1 mm (or in some preferred embodiments 0.9 mm and 1.1 mm) or in still other preferred embodiments of between 1.0 mm and 1.12 mm (or in some preferred embodiments 0.8 mm and 1.12 mm). In some preferred embodiments, plate extension 30 may be 1.0 mm in average thickness or may be from 1.0 mm to 1.2 mm or from 1.0 mm to 1.3 mm or from 1.0 to 1.4 mm in average thickness.

The average thickness of plate extension 30 may not exceed 80% of the average thickness of plate body 20 and therefore may not exceed 1.2 mm or in some other preferred embodiments may not exceed 1.28 mm or 1.3 mm or 1.4 mm or 1.5 mm or may not exceed 1.6 mm.

In some preferred embodiments, plate extension 30 and/or plate body may have a substantially uniform thickness.

As seen in FIG. 6, which shows plate 10 alongside the distal radius, the distal radius fixation plate body 20 may also have an obliquely angled hole such as a recessed screw hole 50 for an elongated attachment member such as a radial column lag screw 55. The obliquely angled recessed screw hole 50 may be situated alongside a proximal portion of a radial styloid fragment in order to stabilize that fragment and avoid having to add additional hardware besides plate 10. Although plate body 20 of is the plate 10 of the present invention may be positioned proximal to the watershed line, it is noted that FIG. 6 is not intended to be precise in regard to showing this particular positioning and the distal end of the plate body 20 may imprecisely appear in FIG. 6 to extend slightly beyond the watershed line.

As shown in FIG. 4, plate extension 30 may have one or two screw holes 33 for small screws to further buttress the plate extension 30 to the ulnar/volar corner.

Plate 10 may be manufactured as a single piece comprising plate body 20 and plate extension 30. Plate 10 may be made of any suitable material, for example it may be made of titanium. The entire plate 10 may be made of the same material. The methods of manufacture of volar plates are well known in the art and may include making the distal radius fixation plate 20 and plate extension 30 as a product of a single unitary mold, in that they are made together as a single unit of the same material.

The present invention may be described as a distal radius fixation plate for volar plating, comprising a distal radius fixation plate body configured to be placed adjacent a fractured volar distal radius and proximal to a watershed line of the volar distal radius; and a distal radius fixation plate extension at least 20% thinner on average than the distal radius fixation plate body and projecting from the distal radius fixation plate body and configured to be placed so that the plate extension extends distal to the watershed line, the plate extension comprising a distal end and a remainder of the plate extension, the distal end of the plate extension configured to curve around and buttress an ulnar/volar corner of the distal radius without curving around other parts of a volar lip of the distal radius, the distal end of the plate extension being a hooked distal end configured to curve more than 90 rotational degrees and up to 120 rotational degrees relative to the remainder of the plate extension so as to curve around and engage the volar lip at the ulnar/volar corner, a continuous width of the hooked distal end configured to engage the volar lip across at least a majority of (in other preferred embodiments, across at least two-thirds, or across all of) the width of the ulnar/volar corner by following a contour of a curve of the volar lip.

The present invention may also be described as a method of volar plate fixation on a fractured distal radius bone. As such, this method may include a step of positioning a distal radius fixation plate body alongside a volar distal radius of the fractured distal radius bone so that the distal radius fixation plate is proximal to the watershed line of the distal radius bone, the distal radius fixation plate having a plate body and a plate extension, the plate extension at least 20% thinner on average than the plate body.

In a further step, the method may also involve anchoring the plate extension to an ulnar volar fragment by positioning the plate extension so that it protrudes distal to the watershed line at the ulnar volar corner of the distal radius bone.

In some preferred embodiments, the method may include a step of having a plate extension that is between 20% to 40% thinner on average than the distal radius plate body protrude distal to the watershed line at the ulnar volar corner. In some preferred embodiments, the method may also include a step of using a hooked end of the plate extension to curve around the ulnar volar corner so as to engage a volar lip of the distal radius. The method may further include positioning the plate extension so that it curves around the ulnar volar corner by more than 90 rotational degrees. This method may also have a step in some preferred embodiments of positioning the plate extension so that it curves around the ulnar volar corner by at least 100 rotational degrees, or so that it curves around the ulnar volar corner by at least 90 rotational degrees and by up to 120 rotational degrees, or so that it curves around the ulnar volar corner by between 95 and 115 degrees or by between 100 and 110 rotational degrees or by between 100 and 120 rotational degrees. It should curve more than 90 rotational degrees This method may also include a further step, in some preferred embodiments, of inserting an elongated attachment member such as a screw into an obliquely angled screw hole on the plate body so as to configure the plate body to further buttress a radial styloid fragment of the fractured distal radius bone. This method may also entail a step of further anchoring the plate extension to the ulnar volar fragment by using a small screw in a screw hole 33 in the plate extension.

The present invention may also be described as a method 200 of method of volar plate fixation on a fractured distal radius. Method 200 may include a step 210 of positioning a distal radius fixation plate body of a distal radius fixation plate alongside a volar distal radius of the fractured distal radius so that the distal radius fixation plate body is proximal to the watershed line of the distal radius, and so that a plate extension that projects from the distal radius fixation plate body and that is at least 20% thinner on average than the plate body, extends distal to the watershed line.

Method 200 may have a further step of positioning the plate extension so as to curve around and buttress the ulnar volar corner of the distal radius without curving around other parts of a volar lip of the distal radius. A further step may comprise positioning the plate extension so as to be anchored to an ulnar volar fragment. Another step may be further anchoring the plate extension to the ulnar volar fragment by using a small locking screw in a screw hole in the plate extension. Another step may be positioning the plate extension so that a distal end of the plate extension, which is a hooked distal end, curves more than 90 rotational degrees, and in some preferred embodiments no more than 115 degrees. Method 200 may also have a step of positioning the plate extension so that the distal end of the plate extension curves around and engages the volar lip at the ulnar volar corner, or of positioning the plate extension so that it curves around the ulnar volar corner by at least 100 rotational degrees, or of positioning the plate extension so that it curves around the ulnar volar corner by at least 90 rotational degrees and by up to 120 rotational degrees, or of positioning the plate extension so that it curves around the ulnar volar corner by between 100 and 110 rotational degrees. The rotational degrees are measured along a curved length that lies on a plane, the plane including longitudinal axis X (see FIG. 4) and being substantially perpendicular to horizontal axis Y (see FIG. 4).

Method 200 may have a step of positioning the plate extension so that a continuous width of the hooked distal end engages the volar lip. A further step may be positioning the plate extension so that the continuous width of the hooked distal end engages the volar lip across at least a majority of a width of the ulnar/volar corner. A step may be positioning the plate extension so that the continuous width of the hooked distal end engages the volar lip across at least 90% of a width of the ulnar/volar corner, or positioning the plate extension so that the continuous width of the hooked distal end engages the volar lip across an entire width of the ulnar/volar corner, or positioning the continuous width of the hooked distal end to span at least two-thirds of a width of the ulnar volar corner. The method 200 may have a step of positioning the continuous width of the hooked distal end to span an entire width of the ulnar/volar corner. A step may be having the continuous width of the hooked distal end engage the volar lip across at least a majority of a width of the ulnar/volar corner by following a contour of a curve of the volar lip without such curving of the hooked distal end extending the hooked distal end into a distal end of the distal radius.

A step may be having the continuous width of the hooked distal end engage the volar lip across at least two-thirds of a width of the ulnar/volar corner by following a contour of a curve of the volar lip without such curving of the hooked distal end extending the hooked distal end into a distal end of the distal radius.

A step may be positioning the plate extension to extend distal to the watershed line at the ulnar volar corner, the plate extension between 30% to 50% thinner on average than the distal radius plate body.

A further step may be screwing a screw into an obliquely angled screw hole on the distal radius fixation plate body so as to configure the distal radius fixation plate body to further stabilize and anchor in place a radial styloid fragment of the fractured distal radius.

The present invention may also be described as a method 300 of manufacturing a distal radius fixation plate. Method 300 may have a step 310 of manufacturing a distal radius fixation plate body and a plate extension of a distal radius fixation plate as one integral product of a mold. Method 300 may have a further step 320 of manufacturing the distal radius fixation plate extension to be at least 20% thinner on average than the distal radius fixation plate body. Another step 330 of method 300 may be manufacturing a continuous width of the hooked distal end to be at least half as wide as the plate extension at any point along a length of the plate extension. A further step 340 may comprise integrally joining a proximal end of the plate extension to at least a third of a width of a distal end of the plate body such that at least a majority of a width of the plate extension is integrally joined to the distal end of the plate body. Method 300 may also have a step 350 of manufacturing the hooked distal end so that the hooked distal end curves more than 90 rotational degrees, and preferably less than 120 rotational degrees, and more preferably less than 115 rotational degrees, and still more preferably between 100 and 115 rotational degrees. The rotational degrees are measured along a curved length that lies on a plane, the plane including longitudinal axis X (see FIG. 4) and being substantially perpendicular to horizontal axis Y (see FIG. 4).

Further steps of method 300 may include integrally joining the most proximal part of the plate extension to a distal end of the plate body at a widest part of the plate extension. Another step of method 300 may be integrally joining the plate extension to the plate body at a distal end of the plate body so that the plate extension projects from the distal end of the plate body along a majority of a rightmost width of a distal end, the rightmost width running from a midpoint of a width of the distal end of the plate body to an ulnar edge of the distal end of the plate body. A further step may involve manufacturing the plate extension so that a continuous width of the hooked distal end is at least two-thirds as wide as the plate extension at any point along a length of the plate extension. Another step may involve manufacturing the plate extension so that the continuous width of the hooked distal end spans an entire width of the plate extension.

The present invention may further be described as a method 400 of volar plate fixation on a fractured distal radius. Method 400 may have a step 410 of positioning a distal radius fixation plate body of a distal radius fixation plate alongside a volar distal radius of the fractured distal radius so that the distal radius fixation plate body is proximal to the watershed line of the distal radius, and so that a plate extension that projects from the distal radius fixation plate body and that is at least 20% thinner on average than the plate body, extends distal to the watershed line. A further step 420 of method 400 may comprise positioning the plate extension so as to curve around and buttress the ulnar volar corner of the distal radius without curving around other parts of a volar lip of the distal radius, the plate extension anchored to an ulnar volar fragment. Method 400 may also have a step 430 of positioning the plate extension so that a continuous width of the hooked distal end of the plate extension curves more than 90 rotational degrees and engages the volar lip across at least a majority of a width of the ulnar/volar corner.

Method 400 may have a further step of positioning the plate extension so that the continuous width of the hooked distal end engages the volar lip across at least 90% of a width of the ulnar/volar corner. A further step of method 400 may be having the continuous width of the hooked distal end engage the volar lip across at least two-thirds of a width of the ulnar/volar corner by following a contour of a curve of the volar lip without such curving of the hooked distal end extending the hooked distal end into a distal end of the distal radius.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method of volar plate fixation on a fractured distal radius, comprising the step of:
   positioning a monolithic distal radius fixation plate comprising a plate body and a plate extension alongside a volar side of the fractured distal radius so (i) the plate body is proximal to a watershed line of the fractured distal radius, and (ii) only the plate extension of the monolithic distal radius fixation plate extends distal to the watershed line of the fractured distal radius,
   wherein,
      the plate extension (i) projects from the plate body, and (ii) is thinner on average than the plate body.

2. The method of claim 1,
   wherein,
      the plate extension is positioned to extend distal to the watershed line at an ulnar volar corner,
      the plate extension is between 30% to 50% thinner on average than the plate body.

3. The method of claim 1, further comprising the step of:
   screwing a screw into an obliquely angled screw hole on the plate body so as to configure the plate body to further stabilize and anchor in place a radial styloid fragment of the fractured distal radius.

4. The method of claim 1,
   wherein,
      the plate extension is at least 20% thinner on average than the plate body.

5. A method of volar plate fixation on a fractured distal radius, comprising the step of:

positioning a monolithic distal radius fixation plate comprising a plate body and a plate extension alongside a volar side of the fractured distal radius so (i) the plate body is proximal to a watershed line of the fractured distal radius, and (ii) the plate extension extends distal to the watershed line of the fractured distal radius, wherein, the plate extension (i) projects from the plate body, (ii) is thinner on average than the plate body, and (iii) is positioned so as to curve around and buttress an ulnar volar corner of the fractured distal radius without curving around any other part of a volar lip of the fractured distal radius, and no other portion of the monolithic distal radius fixation plate curves around any other part of the volar lip of the fractured distal radius.

6. The method of claim 5, wherein the plate extension is positioned so as to be anchored to an ulnar volar fragment.

7. The method of claim 6, further comprising the step of:
further anchoring the plate extension to the ulnar volar fragment by using a small locking screw in a screw hole in the plate extension.

8. The method of claim 6, wherein the plate extension is positioned so that a distal end of the plate extension, which is a hooked distal end, curves more than 90 rotational degrees relative to a remainder of the plate extension.

9. The method of claim 8, wherein the plate extension is positioned so that the distal end of the plate extension curves around and engages the volar lip at the ulnar volar corner.

10. The method of claim 9, wherein the plate extension is positioned so that it curves around the ulnar volar corner by at least 100 rotational degrees.

11. The method of claim 9, wherein the plate extension is positioned so that it curves around the ulnar volar corner by more than 90 rotational degrees and by up to 120 rotational degrees.

12. The method of claim 9, wherein the plate extension is positioned so that it curves around the ulnar volar corner by between 100 and 110 rotational degrees.

13. The method of claim 9, wherein the plate extension is positioned so that it curves around the ulnar volar corner by more than 90 rotational degrees and by up to 115 rotational degrees.

14. The method of claim 9, wherein the plate extension is positioned so that a continuous width of the hooked distal end engages the volar lip.

15. The method of claim 14, wherein the plate extension is positioned so that the continuous width of the hooked distal end engages the volar lip across at least a majority of a width of the ulnar volar corner.

16. The method of claim 14, wherein the plate extension is positioned so that the continuous width of the hooked distal end engages the volar lip across at least 90% of a width of the ulnar volar corner.

17. The method of claim 14, wherein the plate extension is positioned so that the continuous width of the hooked distal end engages the volar lip across an entire width of the ulnar volar corner.

18. The method of claim 15, wherein the continuous width of the hooked distal end is positioned to span at least two-thirds of the width of the ulnar volar corner.

19. The method of claim 15, wherein the continuous width of the hooked distal end is positioned to span an entirety of the width of the ulnar volar corner.

20. The method of claim 15, wherein, the continuous width of the hooked distal end engages the volar lip across at least a majority of the width of the ulnar volar corner by following a contour of a curve of the volar lip without such curving of the hooked distal end extending the hooked distal end into a distal end of the fractured distal radius.

21. The method of claim 15, wherein, the continuous width of the hooked distal end engages the volar lip across at least two-thirds of the width of the ulnar volar corner by following a contour of a curve of the volar lip without such curving of the hooked distal end extending the hooked distal end into a distal end of the fractured distal radius.

22. A method of volar plate fixation on a distal radius, comprising the step of:

positioning a monolithic distal radius fixation plate comprising a plate body and only a single plate extension alongside a volar side of the distal radius so (i) the plate body is proximal to a watershed line of the distal radius, and (ii) the plate extension projects from the plate body and extends distal to the watershed line, wherein, the plate extension is positioned so as to curve around and buttress an ulnar volar corner of the distal radius without curving around other parts of a volar lip of the distal radius, the plate extension anchored to an ulnar volar fragment, and the plate extension is positioned so that a continuous width of a hooked distal end of the plate extension curves more than 90 rotational degrees relative to a remainder of the plate extension and engages the volar lip across at least a majority of a width of the ulnar volar corner.

23. The method of claim 22, wherein, the plate extension is positioned so that the continuous width of the hooked distal end engages the volar lip across at least 90% of the width of the ulnar volar corner.

24. The method of claim 22, wherein, the continuous width of the hooked distal end engages the volar lip across at least two-thirds of the width of the ulnar volar corner by following a contour of a curve of the volar lip without such curving of the hooked distal end extending the hooked distal end into a distal end of the distal radius.

25. The method of claim 22, wherein, the plate extension is at least 20% thinner on average than the plate body.

* * * * *